US006978783B2

(12) United States Patent
Svendsen

(10) Patent No.: US 6,978,783 B2
(45) Date of Patent: Dec. 27, 2005

(54) MANIFOLD

(75) Inventor: Gunnar N. Svendsen, Jyllinge (DK)

(73) Assignee: Unomedical A/S, Lynge (DK)

( * ) Notice: Subject to any disclaimer, the term of this patent is extended or adjusted under 35 U.S.C. 154(b) by 268 days.

(21) Appl. No.: 10/240,884

(22) PCT Filed: Feb. 21, 2001

(86) PCT No.: PCT/DK01/00118

§ 371 (c)(1),
(2), (4) Date: Oct. 4, 2002

(87) PCT Pub. No.: WO01/76659

PCT Pub. Date: Oct. 18, 2001

(65) Prior Publication Data

US 2003/0106559 A1 Jun. 12, 2003

(30) Foreign Application Priority Data

Apr. 6, 2000 (DK) .................................... 2000 00579

(51) Int. Cl.[7] .............................................. A61M 16/00
(52) U.S. Cl. .............................. 128/207.14; 128/207.15
(58) Field of Search ..................... 128/200.24, 207.14, 128/207.15, 207.16, 200.26, 200.27, 912, 205.24; 604/158, 35, 163, 171, 246–249, 905

(56) References Cited

U.S. PATENT DOCUMENTS

| | | |
|---|---|---|
| 3,469,582 A | 9/1969 | Jackson |
| 3,517,669 A | 6/1970 | Buono et al. |
| 3,595,445 A | 7/1971 | Buford et al. |
| 3,902,500 A | 9/1975 | Dryden |
| 3,958,566 A | 5/1976 | Furihata |
| 3,991,762 A * | 11/1976 | Radford ..................... 604/119 |
| 4,180,066 A | 12/1979 | Milliken et al. |
| 4,266,815 A | 5/1981 | Cross |
| 4,287,889 A | 9/1981 | Stupar |
| 4,452,473 A | 6/1984 | Ruschke |
| 4,510,933 A | 4/1985 | Wendt et al. |
| 4,534,542 A | 8/1985 | Russo |
| 4,537,182 A | 8/1985 | Otani |
| 4,561,428 A | 12/1985 | Konomura |
| 4,610,664 A | 9/1986 | Harle |

(Continued)

FOREIGN PATENT DOCUMENTS

| | | |
|---|---|---|
| DE | 1 912 287 | 3/1968 |
| EP | 0349745 A1 | 1/1990 |
| EP | 1208865 A2 | 5/2002 |
| EP | 1210957 A1 | 6/2002 |
| GB | 2123106 A | 1/1984 |
| GB | 2270845 A | 3/1994 |
| WO | WO 93/17742 A1 | 9/1993 |
| WO | WO 93/21981 A2 | 11/1993 |
| WO | WO 95/31240 A1 | 11/1995 |
| WO | WO 95/31250 A1 | 11/1995 |
| WO | WO 96/09082 A1 | 3/1996 |
| WO | WO 96/26757 A1 | 9/1996 |
| WO | WO 96/30069 A1 | 10/1996 |
| WO | WO 98/33536 | 1/1998 |
| WO | WO 98/10808 A2 | 3/1998 |

Primary Examiner—Teena Mitchell
(74) Attorney, Agent, or Firm—Finnegan, Henderson, Farabow, Garrett & Dunner, LLP

(57) ABSTRACT

The invention relates to a manifold (100) for a closed system (1) for endotracheal ventilation and aspiration of a patient, having a first section (115) and a second section (145), an opening (112) configured for allowing influx of a flushing medium to the first section (115), and a passage (118) configured for allowing advancement of the catheter from the first section (115) and into the second section (145). The invention is characterised by a valve body (132) arranged interiorly of the first section (115) and configured for optionally allowing blocking of the passage (118) in a first position and of the opening (112) in a second position.

74 Claims, 5 Drawing Sheets

U.S. PATENT DOCUMENTS

| | | |
|---|---|---|
| 4,638,539 A | 1/1987 | Palmer |
| 4,673,393 A | 6/1987 | Suzuki et al. |
| 4,696,296 A | 9/1987 | Palmer |
| 4,722,366 A | 2/1988 | Maaskamp |
| 4,735,441 A | 4/1988 | Stephens |
| 4,825,859 A | 5/1989 | Lambert |
| 4,834,726 A | 5/1989 | Lambert |
| 4,836,199 A | 6/1989 | Palmer |
| 4,838,255 A | 6/1989 | Lambert |
| 4,846,167 A | 7/1989 | Tibbals |
| 4,850,350 A | 7/1989 | Jackson |
| 4,867,153 A | 9/1989 | Lorenzen et al. |
| 4,872,579 A | 10/1989 | Palmer |
| 4,938,741 A | 7/1990 | Lambert |
| 4,967,743 A | 11/1990 | Lambert |
| 4,981,466 A | 1/1991 | Lumbert |
| 5,009,391 A | 4/1991 | Steigerwald |
| 5,025,806 A | 6/1991 | Palmer et al. |
| 5,060,646 A | 10/1991 | Page |
| 5,065,754 A | 11/1991 | Jensen |
| 5,073,164 A | 12/1991 | Hollister et al. |
| 5,083,561 A | 1/1992 | Russo |
| 5,107,829 A | 4/1992 | Lambert |
| 5,116,088 A | 5/1992 | Bird |
| 5,120,305 A | 6/1992 | Boehringer et al. |
| 5,125,893 A | 6/1992 | Dryden |
| 5,133,345 A | 7/1992 | Lambert |
| 5,134,996 A | 8/1992 | Bell |
| 5,139,018 A | 8/1992 | Brodsky et al. |
| 5,140,983 A | 8/1992 | Jinotti |
| 5,158,569 A | 10/1992 | Strickland et al. |
| 5,163,926 A | 11/1992 | Bailey et al. |
| 5,181,908 A | 1/1993 | Bell |
| 5,184,611 A | 2/1993 | Turnbull |
| 5,215,522 A | 6/1993 | Page et al. |
| 5,220,916 A | 6/1993 | Russo |
| 5,254,098 A | 10/1993 | Ulrich et al. |
| 5,255,676 A | 10/1993 | Russo |
| 5,269,756 A | 12/1993 | Dryden |
| 5,269,768 A | 12/1993 | Cheung |
| 5,277,177 A | 1/1994 | Page et al. |
| 5,279,549 A | 1/1994 | Ranford |
| 5,300,043 A | 4/1994 | Devlin et al. |
| 5,309,902 A | 5/1994 | Kee et al. |
| 5,325,850 A | 7/1994 | Ulrich et al. |
| 5,325,851 A | 7/1994 | Reynolds et al. |
| 5,333,606 A | 8/1994 | Schneider et al. |
| 5,333,607 A | 8/1994 | Kee et al. |
| 5,335,655 A | 8/1994 | Kee |
| 5,337,780 A | 8/1994 | Kee |
| 5,349,950 A | 9/1994 | Ulrich et al. |
| 5,354,267 A | 10/1994 | Niermann et al. |
| 5,355,876 A | 10/1994 | Brodsky et al. |
| 5,368,017 A | 11/1994 | Sorenson et al. |
| 5,377,672 A | 1/1995 | Kee |
| 5,419,769 A | 5/1995 | Devlin et al. |
| 5,433,195 A * | 7/1995 | Kee et al. ............... 128/207.14 |
| 5,445,141 A | 8/1995 | Kee et al. |
| 5,449,348 A | 9/1995 | Dryden |
| 5,456,675 A | 10/1995 | Wolbring et al. |
| 5,460,613 A | 10/1995 | Ulrich et al. |
| 5,487,381 A * | 1/1996 | Jinotti ............... 128/207.14 |
| 5,490,503 A | 2/1996 | Hollister |
| 5,496,287 A | 3/1996 | Jinotti |
| 5,513,628 A | 5/1996 | Coles et al. |
| 5,562,618 A | 10/1996 | Cai et al. |
| 5,579,762 A | 12/1996 | Lee |
| 5,582,161 A | 12/1996 | Kee |
| 5,598,840 A * | 2/1997 | Iund et al. ............... 128/207.14 |
| 5,611,336 A | 3/1997 | Page et al. |
| 5,613,663 A | 3/1997 | Schmidt et al. |
| 5,628,306 A * | 5/1997 | Kee ............... 128/203.12 |
| 5,632,729 A | 5/1997 | Cai et al. |
| 5,636,625 A | 6/1997 | Miyagi et al. |
| 5,642,726 A | 7/1997 | Owens et al. |
| 5,645,048 A | 7/1997 | Brodsky et al. |
| 5,664,564 A | 9/1997 | Palmer |
| 5,664,594 A | 9/1997 | Kee |
| 5,669,380 A | 9/1997 | Garry et al. |
| 5,676,136 A | 10/1997 | Russo |
| 5,694,922 A | 12/1997 | Palmer |
| 5,702,374 A | 12/1997 | Johnson |
| 5,730,123 A | 3/1998 | Lorenzen et al. |
| 5,735,271 A * | 4/1998 | Lorenzen et al. ...... 128/207.16 |
| 5,738,091 A | 4/1998 | Kee et al. |
| 5,775,325 A * | 7/1998 | Russo ............... 128/205.12 |
| 5,779,687 A | 7/1998 | Bell et al. |
| 5,791,337 A | 8/1998 | Coles et al. |
| 5,794,986 A | 8/1998 | Gansel et al. |
| 5,827,218 A | 10/1998 | Nguyen et al. |
| 5,830,214 A | 11/1998 | Flom et al. |
| 5,855,562 A | 1/1999 | Moore et al. |
| 5,864,938 A | 2/1999 | Gansel et al. |
| 5,919,174 A * | 7/1999 | Hanson ............... 604/283 |
| 5,993,437 A | 11/1999 | Raoz |
| 6,012,451 A | 1/2000 | Palmer |
| 6,070,582 A * | 6/2000 | Kee ............... 128/207.16 |
| 6,135,110 A | 10/2000 | Roy |
| 6,148,857 A | 11/2000 | West et al. |
| 6,190,372 B1 | 2/2001 | Racz |
| 6,227,200 B1 | 5/2001 | Crump et al. |
| 6,254,061 B1 | 7/2001 | Levine et al. |
| 6,254,589 B1 | 7/2001 | Raoz |
| 6,415,789 B1 * | 7/2002 | Freitas et al. ........... 128/202.27 |
| 6,447,473 B1 * | 9/2002 | Levine et al. ............ 604/33 |
| 6,494,203 B1 | 12/2002 | Palmer |
| 6,543,451 B1 * | 4/2003 | Crump et al. ........... 128/207.14 |
| 6,575,944 B1 | 6/2003 | McNary et al. |
| 6,584,970 B1 * | 7/2003 | Crump et al. ........... 128/200.24 |
| 6,588,425 B2 * | 7/2003 | Rouns et al. ........... 128/207.14 |
| 6,588,427 B1 * | 7/2003 | Carlsen et al. ......... 128/207.14 |
| 6,602,219 B2 | 8/2003 | Madsen et al. |
| 6,609,520 B1 * | 8/2003 | Carlsen et al. ......... 128/207.14 |
| 6,612,304 B1 * | 9/2003 | Cise et al. ............. 128/200.26 |
| 6,615,835 B1 * | 9/2003 | Cise et al. ............. 128/207.14 |
| 2001/0029953 A1 | 10/2001 | Neto et al. |
| 2001/0044600 A1 | 11/2001 | Elkins |
| 2003/0047704 A1 | 3/2003 | Svendsen |
| 2003/0056787 A1 | 3/2003 | Svendsen |
| 2003/0106558 A1 | 6/2003 | Cardon |
| 2003/0106559 A1 | 6/2003 | Svendsen |

* cited by examiner

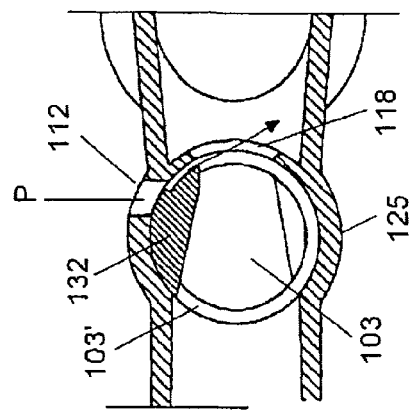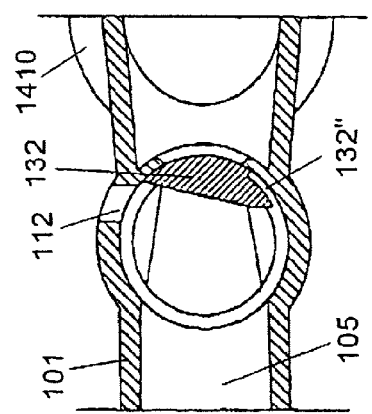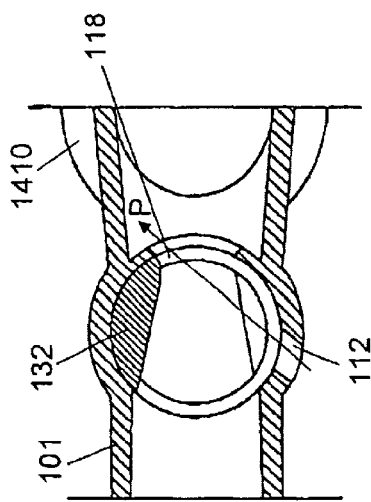
Fig. 5a
Fig. 5b
Fig. 5c

MANIFOLD

This application claims priority to PCT/DK01/00118, filed Feb. 21, 2001, published under PCT Article 21(2) in English, which in turn claims priority to Danish Application PA 2000 00579, filed Apr. 6, 2000, the entirety of these references are incorporated herein.

The present invention relates to a manifold for a closed system for endotrachael ventilation and aspiration of a patient, which manifold has an interior manifold chamber that defines a through-going axis through the manifold and a system for endotrachael ventilation of a patient comprising a catheter that extends interiorly of a collapsible shrouding, the system further comprising a first end connected to a vacuum source, and a second end connected to a manifold.

BACKGROUND

For instance, international patent application No WO98/33536 and U.S. Pat. No. 5,487,381 teach various types of manifolds.

U.S. Pat. No. 5,354,267, by reference incorporated herein in its entirety, discloses a manifold for a closed system for endotracheal ventilation and aspiration of a patient, which manifold has an interior manifold chamber that defines a through-going axis through the manifold. This manifold suffers from a number of inconveniences as regards manufacturing techniques and use. Among others, the prior art manifold does not enable supply of a fluid to the patient via the manifold while simultaneously the patient's respirator tracts are sucked by means of a catheter advanced through the manifold. Thus, the invention aims to provide an improved manifold that can be manufactured in an inexpensive manner and that allows adjustment of a wide variety of operating states.

BRIEF SUMMARY OF THE INVENTION

The improved manifold is obtained in that the valve body is configured as a segment of the face of a cylinder configured for abutting on the cylindrical portion. When desired, the described configuration of the valve body thus enables flushing of a first section of the manifold chamber without significant risk of the flushing fluid unintentionally penetrating into the second section of the manifold chamber that is in direct communication with the patient. Besides the invention enables an embodiment in which it is possible, in one of its operating states, to block the manifold relative to the supply source for the flushing fluid whereby the risk of unintentional influx of flushing fluid is to a large extent prevented when suction is performed on the patient's respiratory tracts.

By an embodiment including a circular guide track for the valve body interior to the first manifold portion and an embodiment wherein the valve body includes an extreme end and the guide track is configured for receiving the extreme end, the valve body can be caused to cooperate with the manifold chamber in a particularly simple manner for blocking the respective openings.

Additional embodiments of the manifold of the present invention allow supply of fluid to the patient while simultaneously a suction operation is performed by means of the catheter.

In another embodiment, the manifold can be constructed by means of a number of separate components that are connected to each other. Also, the manifold may comprise a peripheral surface area and a bushing, whereby shrouding for the catheter can be secured to the manifold.

BRIEF DESCRIPTION OF SEVERAL VIEWS OF THE DRAWINGS

The invention will now be explained in further detail with reference to the embodiments shown in the drawings.

FIGS. 5 a–c are schematical views of two other embodiments of the invention, seen in a cross sectional view along the line V in FIG. 2.

DETAILED DESCRIPTION OF THE INVENTION

Figure 1:
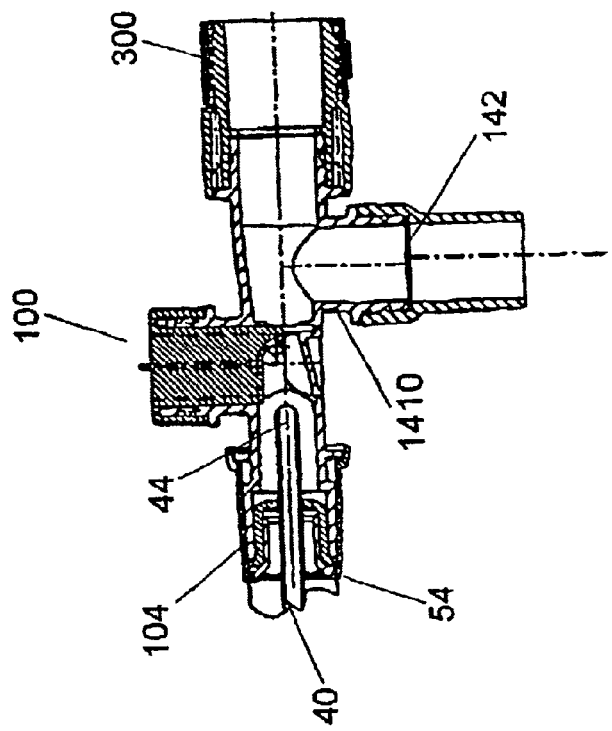
FIG. 1 shows a part of a system for endotracheal ventilation of a patient.
Figure 1:
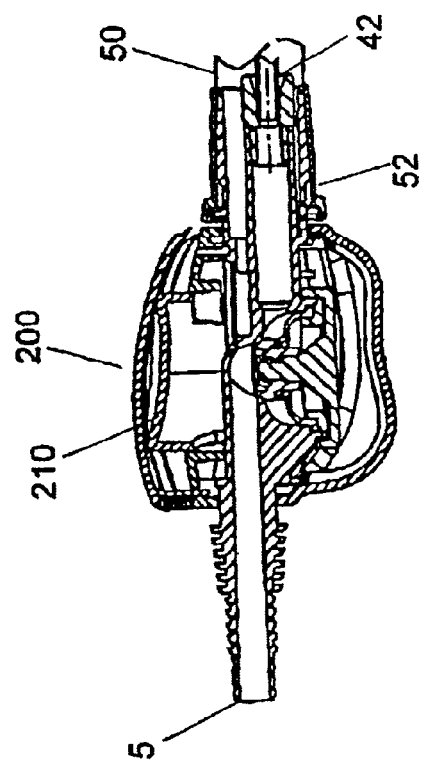

In principle, the mode of operation of the system shown in FIG. 1 corresponds to eg the mode of operation of the system described in Danish patent application No. 32/95. A flexible shrouding or pipe coupling 50 is thus, at its first end 52, coupled to a valve housing 200 and, at its other end 54, coupled to a manifold 100 according to the invention. Via a coupling 5, the valve housing 200 is configured for being connected to a not shown suction device for providing a sub-atmospheric pressure within the system. The manifold 100, which is preferably transparent, is configured for being—via a coupling 300—connected to a tubular member or 'tube' for endotracheal ventilation of a patient, ie a tubular member that is configured for being introduced into the respiratory tracts of the patient with a view to maintaining artificial ventilation of that patient. A ventilation stub 1410 allows ventilation of the patient by means of a not shown conventional apparatus.

Additionally and in a conventional manner, the system shown in FIG. 1 comprises a catheter 40 that extends into the interior of the shrouding 50 and that can be introduced into the respiratory tracts of the patient for drawing out secretion. At its first end 42, the catheter 40 is securely connected to the valve housing 200 and, at its opposite end 44, it is displaceably received in the manifold 100, the catheter being, via a packing 104, sealed relative to the shrouding 50, which means that fluid cannot penetrate into the shrouding. The packing 104 also causes secretion to be scraped off the outside of the catheter 40 during withdrawal of the catheter from the patient. It will be understood that the opposite end 44 of the catheter forms a suction point that can, during simultaneous folding of the shrouding 50, be displaced through the interior of the manifold 100 and into the not shown hose for ventilation of the patient. By this movement, the end 44 of the catheter is thus moved to the right in FIG. 1. Hereby it is possible to perform regular suction of secretion from the patient's respiratory tracts by the operator connecting the system to the suction device by operating a valve button 210 in the valve housing 200.

Figure 2:
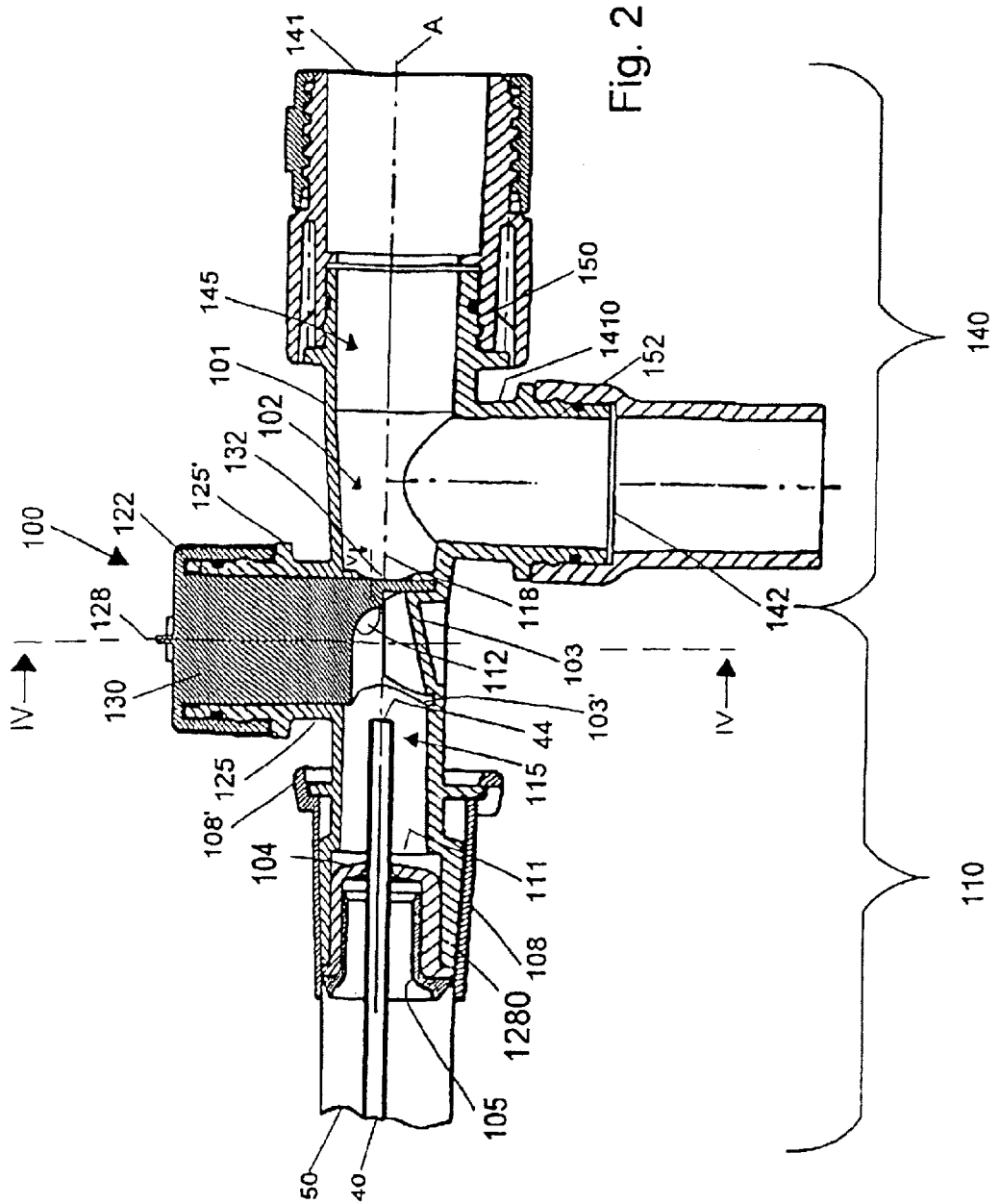
FIG. 2 shows a manifold according to the invention, in a cross sectional view and featuring an exemplary valve body.

FIG. 2 shows further constructive details of the manifold 100 according to the invention. In general terms, the manifold is formed of a manifold wall 101 that defines an interior, elongate manifold chamber 102. A first part 110 of the manifold 100 forms a first section 115 of the manifold chamber 102, while a second part 140 of the manifold 100 forms a second section 145 of the manifold chamber 102. The manifold chamber 102 defines a through-going axis A that extends in extension of the catheter 40 and the shrouding 50 that is outlined to the left in the drawing. It will appear that the manifold wall 101 forms an elongate head part for the manifold 100, which head part is extends along the axis A and is interrupted by a cylindrical portion 125 in the first manifold part 110, which part extends transversally to the axis A. The ventilation stub 1410 mentioned above is arranged in the other manifold part 140. The cylindrical portion 125 has a central axis 128 that preferably extends perpendicular to the axis A. The elongate head part is preferably configured as a cylindrical body manufactured by being cast integrally with the cylindrical portion 125 and the ventilation stub 1410.

To the left in FIG. 2, the manifold 100 has a first opening (gate) 111, through which the catheter 40 can be introduced into the manifold 100. Opposite the opening 111 the manifold 100 has a second opening (gate) 141 for the introduction of the catheter into the patient's respiratory tracts. The ventilation stub 1410 forms a third opening (gate) 142 for the manifold 100 whereby gas is allowed to travel from the third opening 142 towards the second opening 141, and vice versa.

Additionally, the manifold 100 has a fourth opening (gate) 112 that allows introduction of a flushing fluid into the manifold chamber 102, the packing 104 preventing influx of flushing fluid into the shrouding 50. Flushing fluid can by conveyed from a not shown supply source to the fourth opening 112 of the manifold 100 via a connector element, generally designated by the reference numeral 160 in FIG. 3, and that may comprise a valve arrangement. It will appear from FIG. 3 that preferably said fourth opening 112 is in connection with a stub 113 that forms a lateral branch extending from the manifold 100.

More specifically the fourth opening 112 is formed in an area of the manifold wall 101 in the cylindrical portion 125 in a level that coincides with, or approximately coincides with, the axis A. It will be understood that said flushing fluid serves the purpose of cleaning the suction point 44 of the catheter 40 and the packing 104 in the position of the catheter 40 shown in FIG. 2, flushing fluid advanced via the opening 112 being sucked out of the manifold chamber 102 by activation of the suction device, ie through the catheter 40.

Besides, the cylindrical portion 125 forms a fifth opening (gate) 122 in the manifold 100. This opening 122 is intended for the mounting within the interior of the cylindrical portion 125 of a turnable cylindrical valve 130 with a valve body 132 that is shown in further detail in FIG. 3. It will appear from FIG. 3 that the valve body 132 is configured as a segment of the face of a cylinder that extends from a cylindrical base part that cooperates with the segment to form the valve 130.

It will be understood that at the transition between the first section 115 and the second section 145, an area will appear whereto the valve body 132 can be turned in a first position. In the following this area will be designated "the passage" 118. The passage 118 may have any expanse along the axis A and also transversally to the axis A; by the solution shown in FIG. 2 the passage can be perceived as that part of the manifold chamber 102 that extends from the valve body 132 to the ventilation stub 1410. The function of this passage is merely to provide access for the catheter to the second section 145 of the manifold chamber 102.

The valve body 132 has a peripheral expanse that is sufficient for the valve, in its first position, to cover the entire expanse of the passage 118 transversally to the axis A and for the valve, in the embodiment shown, to block the fourth opening 112 in a second position. The valve body 132 has an end 132' opposite the cylindrical base part.

The valve 130 shown in FIG. 2 is in the first position. It is usually desired to maintain the described blocking of the first section 115 from the second section 145 while ventilation of the patient is performed via the ventilation stub 1410 without suction of the patient with the catheter 40. Besides, exactly in this position it is possible to supply flushing fluid for cleaning the suction point 44 and secretion that is scraped off by means of the packing 104 and that has thus collected in the first section 115 of the manifold chamber 102. The flushed-off secretion is conveyed along with the flushing fluid out through the catheter 40 as explained above. In this context, it is advantageous that, in the first position of the valve 130, influx of flushing fluid into the second section 145 is avoided.

From said first position the valve 130 can be turned about 90° in a first direction to said second position, in which the first 115 and the second 145 sections of the manifold chamber 102 are in communication with each other, and wherein the catheter 40 can be advanced from the left to the right in FIG. 2. In the exemplary embodiment the valve body 132 is located opposite the fourth opening 112 in said second position and thereby cuts off the fourth opening 112, with the result that, to a wide extent, it is possible to prevent influx of flushing fluid into the manifold chamber 102. Said second position of the valve body 132 is outlined in FIG. 3 where the valve has been displaced outwards from the cylindrical portion 125. Turning of the valve in the direction opposite said first direction makes it possible to advance fluid while simultaneously performing a suction of the patient's respiratory tracts.

As mentioned the valve 130 is configured for being able to turn interiorly of the cylindrical portion 125, and to this end the cylindrical base portion of the valve 130 is provided with an operating face that the user can seize with a finger. The valve can be received in close abutment on the interior surface of the cylindrical portion 125 and secured to the cylindrical portion 125 by means of suitable, complementary securing means 125', eg by being clicked into position. Said securing means 125' that can be arranged on the outside of the cylindrical portion 125 preferably comprise a turning constrictor whereby the valve can be turned only between extreme positions that define the above-mentioned first and second positions. In the embodiment shown the extreme positions correspond to a turning of the valve of about 90°. Thereby it is possible to avoid unintentional supply of flushing fluid while in a position where the passage 118 is open.

It is possible to provide a solution whereby influx of flushing fluid through the fourth opening 112 is not possible until the valve body 132 configured as the aforementioned segment cuts off the passage 118 completely, ie when the segment has been turned through a given angle about the axis 128 in a direction towards the passage 118. This presupposes a mutual adaptation of the following parameters: The angulation of the opening 112 about the axis 128 relative to the passage 118, the peripheral expanse of the segment 132, and the allowed turning movement of the valve 130.

Figure 4:
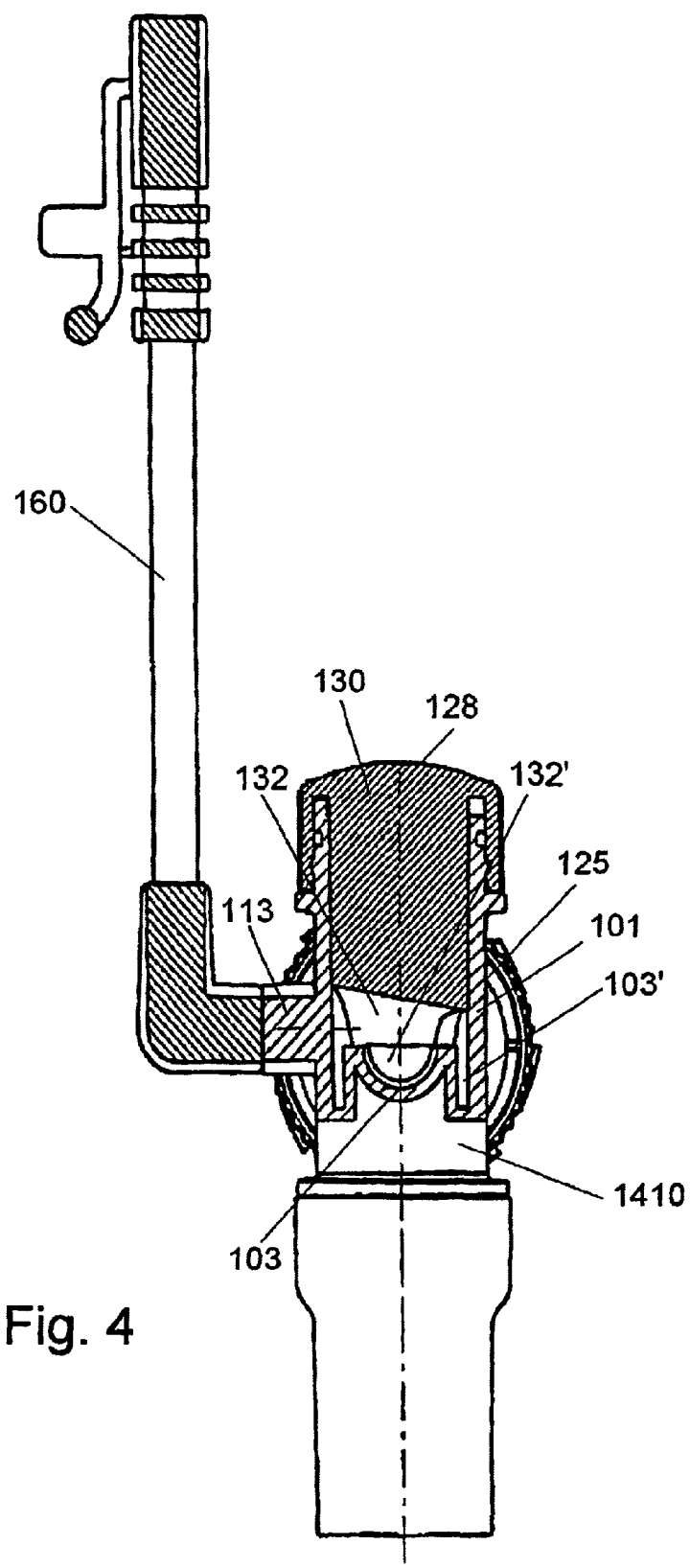
FIG. 4 is a cross sectional view along the line IV—IV shown in FIG. 2.

FIGS. 2 and 4 also show that, on the inside of the manifold wall 101 opposite the fifth opening 122 an elevated portion 103 is arranged that combines with the manifold wall 101 to define a circular guide track 103' for the extreme end 132' of the valve body 132. The track 103' is thereby delimited by the interior surface of the cylindrical portion 125 and the exterior surface of the elevated portion 103, respectively, and thereby serves to ensure reliable conveyance of the valve body 132. The elevated portion 103 extends with a certain inclination towards the passage in order to thereby ensure reliable conveyance of the catheter while the latter is advanced through the manifold.

Figure 3:
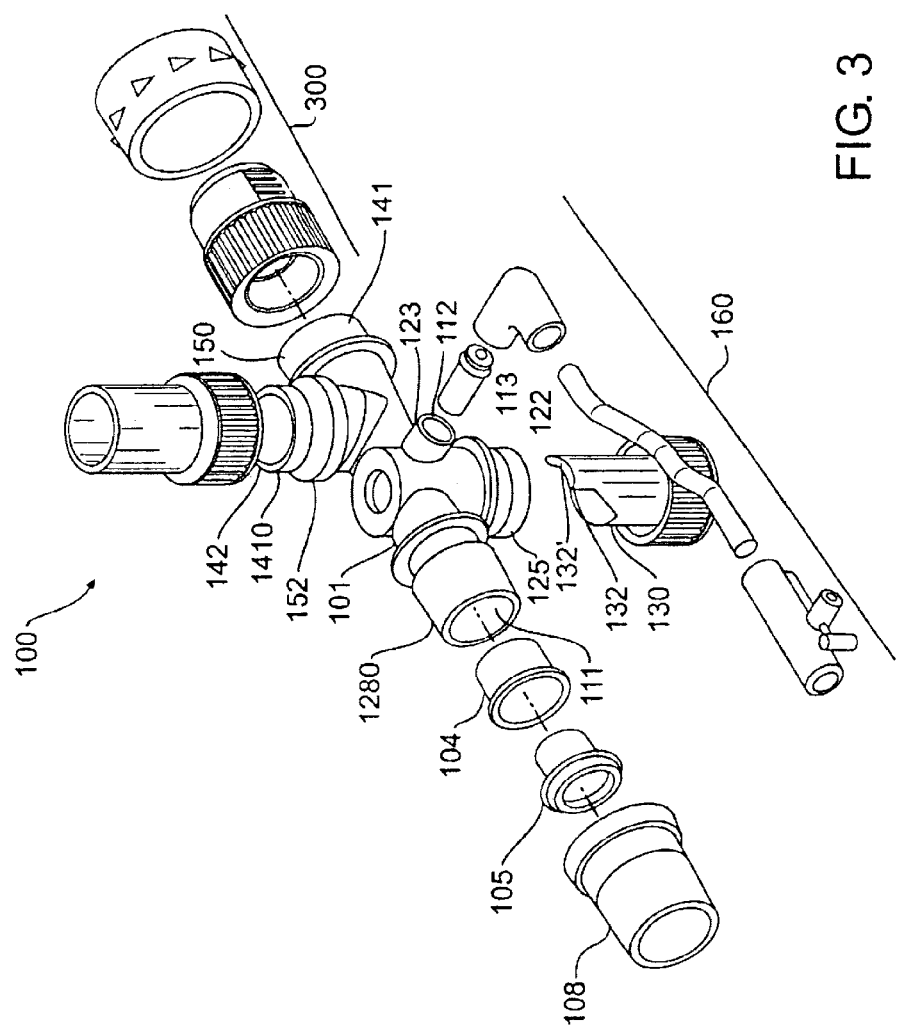
FIG. 3 shows the manifold shown in FIG. 2 in an exploded view, seen from the opposite side.

From FIG. 3 it will appear more clearly that the first manifold portion 110 is provided with a packing 104 having a central, through-going opening that forms a close abutment on the catheter 40. The packing 104 is secured in abutment against the interior surface of a peripheral surface area 1280 of the first manifold portion 110 in the area at the first opening 111. More specifically, the packing 104 is secured by means of an concealed sleeve 105 that is enclosed by the packing 104 and that may have a conical shape whereby pressing-in of the concealed sleeve 105 generates a pressure that is oriented radially from the axis A and ensures reliable securing of the packing 104. To secure the concealed sleeve 105, the manifold 100 is also provided with a sleeve 108 that comprises clicking means 108' whereby the sleeve 108 can be secured against being pulled off the manifold 100. Between the peripheral surface area 1280 and the inside of the sleeve 108 an annular chamber is preferably provided, in which the end 54 of the shrouding 50 is received and secured.

It will be understood that the ventilation stub 1410 can preferably be provided with a screw thread 152 for coupling of a ventilation apparatus thereto. Also, a thread 150 can be arranged on the outside of the manifold wall 101 at the second opening 141 with a view to mounting of a coupling kit for an endotracheal tube, eg of the kind described in the applicant's co-pending patent application.

FIGS. 5a and 5b show an alternative embodiment of the invention wherein the extreme end 132' of the valve body 132 is received in the circular guide track 103'. The first position of the valve 130 shown in FIG. 5a corresponds to the position shown in FIG. 2. It will appear that the fourth opening 112 is exposed and that, to a wide extent, a medium supplied is unable to flow into the second manifold section 145. FIG. 5b shows a second position of the valve 130, wherein the passage 118 is open. In this embodiment, the segment forming valve body 132 is provided with a recess 132" that extends across a part of the side that faces towards the surface of the cylindrical portion 125. The recess 132" is configured such that fluid supplied via the opening 112 will be directionally oriented towards the passage 118 in the second position of the valve 130 shown in FIG. 5b, as indicated by the arrow P. Hereby it is possible to introduce the catheter through the passage 118 and to perform a suction of the patient while simultaneously fluid is supplied to the patient via the fourth opening 112. Such option is desirable in certain cases to provoke a coughing attack and thus release secretion that is removed by sucking by means of the catheter.

FIG. 5c illustrates a third embodiment of the invention, wherein the extreme end 132' of the valve body 132 has been received in the circular track 103' and wherein the valve body 132 is configured as shown in FIGS. 2–4. It will appear that in this embodiment the fourth opening of the manifold 112 is arranged offset opposite the passage 118 whereby, when the valve 130 is conveyed to the shown second position opposite the opening 112, it is also ensured that fluid supplied via the opening 112 will be directionally oriented towards the passage 118, as indicated by the arrow P, while simultaneously a catheter can be conveyed through the passage 118. The valve 130 may be turned to the first position shown in FIG. 2, and optionally to a further-third position, wherein the segment forming valve body 132 is positioned in front of the opening 112 in order to prevent, to the widest possible extent, unintentional influx of fluid.

Albeit in the present text the guide track 103' is described as annular, the person skilled in the art will appreciate that the guide track 103' does not necessarily have to extend continuously around the interior surface of the cylindrical portion 125.

What is claimed is:

1. A manifold (100) for a closed system (1) for endotracheal ventilation and aspiration of a patient, which manifold (100) has an interior manifold chamber (102) that defines a through-going axis through the manifold (100), and comprises:
    a first manifold portion (110) defining a first section (115) of the manifold chamber (102);
    a second manifold portion (140) arranged in extension of said first manifold portion (110) and defining a second section (145) of the manifold chamber (102);
    a first opening (111) arranged in the first manifold section (110) and configured for allowing advancement of a catheter for aspiration of the patient into the first section (115);
    a second opening (141) arranged in the second manifold portion (140) opposite said first opening (111) and configured for allowing advancement of the catheter from the second section (145), preferably to an endotracheal tube;
    a third opening (142) arranged in the second manifold portion (140) and configured for allowing ventilation of the patient;
    a passage (118) arranged opposite said first opening (111) and configured for allowing advancement of the catheter from the first section (115) and into the second section (145);
    a turnable valve body (132) arranged interiorly of the first section (115) and configured for being movable between a first position in which the passage (118) is blocked and a second position;
    wherein the first manifold portion (110) also defines a substantially cylindrical portion (125) that extends substantially perpendicular to the axis;
    which cylindrical portion (125) has a cylinder axis (128) about which said valve body (132) is able to turn between the first and the second position;
    a fourth opening (112) arranged in the cylindrical portion (125) and configured for allowing supply of fluid; characterised in that the valve body (132) is configured as a segment of a face of a cylinder configured for abutting on the cylindrical portion (125); and
    a circular guide track (103") for the valve body (132) interior to the first manifold portion (110).

2. A manifold according to claim 1, wherein the valve body (132) further comprises an extreme end (132'); and
    the guide track (103') is configured for receiving the extreme end (132').

3. A manifold according to claim 2, wherein the valve body (132) is configured such that the fourth opening (112) is open in said first position of the valve body (132).

4. A manifold according to claim 2, wherein the valve body (132) is configured such that the passage (118) and the fourth opening (112) are open in said second position; and
    the segment (132) further comprises a guide face (132") configured for conveying the fluid supply from the fourth opening (112) in a direction through the passage (118).

5. A manifold according to claim 2, wherein the valve body (132) is configured such that the passage (118) and the fourth opening (112) are open in said second position; and
the fourth opening (112) is so arranged relative to the passage (118) that the supplied fluid flows through the passage (118).

6. A manifold according to claim 1, wherein the valve body (132) is configured such that the fourth opening (112) is open in said first position of the valve body (132).

7. A manifold according to claim 1, wherein the valve body (132) is configured such that the passage (118) and the fourth opening (112) are open in said second position; and
the segment (132) further comprises a guide face (132") configured for conveying the fluid supply from the fourth opening (112) in a direction through the passage (118).

8. A manifold according to claim 7, wherein the guide face (132") forms a flow passage in combination with an interior face of the manifold (100).

9. A manifold according to claim 1, wherein the valve body (132) is configured such that the passage (118) and the fourth opening (112) are open in said second position; and
the fourth opening (112) is so arranged relative to the passage (118) that the supplied fluid flows through the passage (118).

10. A manifold (100) according to claim 1, wherein the interior manifold chamber (102) is configured as a cylindrical body interrupted by the cylindrical portion (125) that extends transversally to the axis.

11. A manifold (100) according to claim 1, wherein the first manifold portion (110) is formed integrally with the second manifold portion (140); and
the passage (118) is defined by an area that is shared by the first section (115) and the second section (145).

12. A manifold (100) according to claim 1, wherein the first manifold portion (110) and the second manifold portion (140) constitute separate portions of the manifold;
the first manifold portion (110) and the second manifold portion (140) comprise mutually complementary connecting means (110', 141'); and
said complementary connecting means (110', 140') form a tight connection.

13. A manifold (100) according to claim 1, wherein, at the first opening (111), the first manifold portion (110) further comprises a peripheral surface area (1280) configured for forming a direct abutment for a compressible shrouding (50) for the catheter (40); and
the manifold (100) further comprises a sleeve (108) configured for securing the shrouding in abutment on said surface (1280).

14. A manifold (100) according to claim 1, wherein the first manifold portion (110) and the second manifold portion (140) further comprises means (150,152), whereby it is possible to directly connect, at the second opening (141), the third opening (142) and the fourth opening (112), an endotracheal tube, a tube for ventilating the patient and a tubing for the supply of fluid, respectively.

15. A manifold according to claim 1, wherein the valve body (132) is configured such that the fourth opening (112) is open in said first position of the valve body (132).

16. A manifold according to claim 1, wherein the valve body (132) is configured such that the passage (118) and the fourth opening (112) are open in said second position; and
the segment (132) further comprises a guide face (132") configured for conveying the fluid supply from the fourth opening (112) in a direction through the passage (118).

17. A manifold according to claim 1, wherein the valve body (132) is configured such that the passage (118) and the fourth opening (112) are open in said second position; and
the fourth opening (112) is so arranged relative to the passage (118) that the supplied fluid flows through the passage (118).

18. A manifold (100) for a closed system (1) for endotracheal ventilation and aspiration of a patient, which manifold (100) has an interior manifold chamber (102) that defines a through-going axis through the manifold (100), said manifold comprising:
a first manifold portion (110) defining a first section (115) of the manifold chamber (102);
a second manifold portion (140) arranged in extension of said first manifold portion (110) and defining a second section (145) of the manifold chamber (102);
a first opening (111) arranged in the first manifold section (110) and configured for allowing advancement of a catheter for aspiration of the patient into the first section (115);
a second opening (141) arranged in the second manifold portion (140) opposite said first opening (111) and configured for allowing advancement of the catheter from the second section (145), preferably to an endotracheal tube;
a third opening (142) arranged in the second manifold portion (140) and configured for allowing ventilation of the patient;
a passage (118) arranged opposite said first opening (111) and configured for allowing advancement of the catheter from the first section (115) and into the second section (145);
a turnable valve body (132) arranged interiorly of the first section (115) and configured for being movable between a first position in which the passage (118) is blocked and a second position;
wherein the first manifold portion (110) also defines a substantially cylindrical portion (125) that extends substantially perpendicular to the axis;
which cylindrical portion (125) has a cylinder axis (128) about which said valve body (132) is able to turn between the first and the second position; a fourth opening (112) arranged in the cylindrical portion (125) and configured for allowing supply of fluid; characterised in that the valve body (132) is configured as a segment of a face of a cylinder configured for abutting on the cylindrical portion (125); and a fifth opening (122) arranged in the cylindrical portion (125);
wherein the valve body (132) is connected to the exterior of the manifold chamber (102) via the fifth opening (122).

19. A system (1) for endotracheal ventilation and aspiration of a patient comprising a catheter (40) that extends interiorly of a collapsible shrouding (50), said system further comprising a first end (52) connected to a vacuum source, and a second end (54) connected to a manifold (100) having an interior manifold chamber (102) that defines a through-going axis through the manifold (100), said manifold (100) comprising:
a first manifold portion (110) defining a first section (115) of the manifold chamber (102);
a second manifold portion (140) arranged in extension of said first manifold portion (110) and defining a second section (145) of the manifold chamber (102);
a first opening (111) arranged in the first manifold section (110) and configured for allowing advancement of a catheter for aspiration of the patient into the first section (115);

a second opening (141) arranged in the second manifold portion (140) opposite said first opening (111) and configured for allowing advancement of the catheter from the second section (145), preferably to an endotracheal tube;

a third opening (142) arranged in the second manifold portion (140) and configured for allowing ventilation of the patient;

a passage (118) arranged opposite said first opening (111) and configured for allowing advancement of the catheter from the first section (115) and into the second section (145);

a turnable valve body (132) arranged interiorly of the first section (115) and configured for being movable between a first position in which the passage (118) is blocked and a second position;

wherein the first manifold portion (110) also defines a substantially cylindrical portion (125) that extends substantially perpendicular to the axis;

which cylindrical portion (125) has a cylinder axis (128) about which said valve body (132) is able to turn between the first and the second position;

a fourth opening (112) arranged in the cylindrical portion (125) and configured for allowing supply of fluid; characterised in that the valve body (132) is configured as a segment of a face of a cylinder configured for abutting on the cylindrical portion (125); and a circular guide track (103") for the valve body (132) interior to the first manifold portion (110).

20. The system (1) according to claim 19, wherein the valve body (132) further comprises an extreme end (132'); and the guide track (103') is configured for receiving the extreme end (132').

21. The system (1) according to claim 19, wherein the valve body (132) is configured such that the fourth opening (112) is open in said first position of the valve body (132).

22. The system (1) according to claim 21, wherein the valve body (132) is configured such that the fourth opening (112) is open in said first position of the valve body (132).

23. The system (1) according to claim 21, wherein the valve body (132) is configured such that the passage (118) and the fourth opening (112) are open in said second position; and the segment (132) further comprises a guide face (132") configured for conveying the fluid supply from the fourth opening (112) in a direction through the passage (118).

24. The system (1) according to claim 21, wherein the valve body (132) is configured such that the passage (118) and the fourth opening (112) are open in said second position; and the fourth opening (112) is so arranged relative to the passage (118) that the supplied fluid flows through the passage (118).

25. The system (1) according to claim 19, wherein the valve body (132) is configured such that the passage (118) and the fourth opening (112) are open in said second position; and the segment (132) further comprises a guide face (132") configured for conveying the fluid supply from the fourth opening (112) in a direction through the passage (118).

26. The system (1) according to claim 25, wherein the guide face (132") forms a flow passage in combination with an interior face of the manifold (100).

27. The system (1) according to claim 19, wherein the valve body (132) is configured such that the passage (118) and the fourth opening (112) are open in said second position; and the fourth opening (112) is so arranged relative to the passage (118) that the supplied fluid flows through the passage (118).

28. The system (1) according to claim 19, wherein the interior manifold chamber (102) is configured as a cylindrical body interrupted by the cylindrical portion (125) that extends transversally to the axis.

29. The system (1) according to claim 19, wherein the first manifold portion (110) is formed integrally with the second manifold portion (140); and the passage (118) is defined by an area that is shared by the first section (115) and the second section (145).

30. The system (1) according to claim 19, wherein the first manifold portion (110) and the second manifold portion (140) constitute separate portions of the manifold;

the first manifold portion (110) and the second manifold portion (140) comprise mutually complementary connecting means (110', 141'); and said complementary connecting means (110', 140') form a tight connection.

31. The system (1) according to claim 19, wherein, at the first opening (111), the first manifold portion (110) further comprises a peripheral surface area (1280) configured for forming a direct abutment for a compressible shrouding (50) for the catheter (40); and the manifold (100) further comprises a sleeve (108) configured for securing the shrouding in abutment on said surface (1280).

32. The system (1) according to claim 19, wherein the first manifold portion (110) and the second manifold portion (140) further comprises means (150,152), whereby it is possible to directly connect, at the second opening (141), the third opening (142) and the fourth opening (112), an endotracheal tube, a tube for ventilating the patient and a tubing for the supply of fluid, respectively.

33. The system (1) according to claim 19 further comprising a fifth opening (122) arranged in the cylindrical portion (125);

wherein the valve body (132) is connected to the exterior of the manifold chamber (102) via the fifth opening (122).

34. The system (1) according to claim 19, wherein the valve body (132) is configured such that the fourth opening (112) is open in said first position of the valve body (132).

35. The system (1) according to claim 19, wherein the valve body (132) is configured such that the passage (118) and the fourth opening (112) are open in said second position; and the segment (132) further comprises a guide face (132") configured for conveying the fluid supply from the fourth opening (112) in a direction through the passage (118).

36. The system (1) according to claim 19, wherein the valve body (132) is configured such that the passage (118) and the fourth opening (112) are open in said second position; and the fourth opening (112) is so arranged relative to the passage (118) that the supplied fluid flows through the passage (118).

37. A manifold (100) for a closed system (1) for endotracheal ventilation and aspiration of a patient, which manifold (100) has an interior manifold chamber (102) that defines a through-going axis through the manifold (100), and comprises;
   a first manifold portion (110) defining a first section (115) of the manifold chamber (102);
   a second manifold portion (140) arranged in extension of said first manifold portion (110) and defining a second section (145) of the manifold chamber (102);
   a first opening (111) arranged in the first manifold section (110) and configured for allowing advancement of a catheter for aspiration of the patient into the first section (115);
   a second opening (141) arranged in the second manifold portion (140) opposite said first opening (111) and configured for allowing advancement of the catheter from the second section (145), preferably to an endotracheal tube;
   a third opening (142) arranged in the second manifold portion (140) and configured for allowing ventilation of the patient;
   a passage (118) arranged opposite said first opening (111) and configured for allowing advancement of the catheter from the first section (115) and into the second section (145);
   a turnable valve body (132) arranged interiorly of the first section (115) and configured for being movable between a first position in which the passage (118) is blocked and a second position;
   wherein the first manifold portion (110) also defines a substantially cylindrical portion (125) that extends substantially perpendicular to the axis;
   which cylindrical portion (125) has a cylinder axis (128) about which said valve body (132) is able to turn between the first and the second position;
   a fourth opening (112) arranged in the cylindrical portion (125) and configured for allowing supply of fluid; characterised in that the valve body (132) is configured as a segment of a face of a cylinder configured for abutting on the cylindrical portion (125);
   said valve body (132) being configured such that the passage (118) and the fourth opening (112) are open in said second position to allow fluid supplied through said fourth opening (112) to flow through said passage (118) while performing suctioning of the patient by said catheter (40) advanced through said passage (118).

38. The manifold (100) according to claim 37, further comprising a circular guide track (103") for the valve body (132) interior to the first manifold portion (110).

39. The manifold (100) according to claim 38, wherein the valve body (132) further comprises an extreme end (132'); and
   the guide track (103') is configured for receiving the extreme end (132').

40. The manifold (100) according to claim 39, wherein the valve body (132) is configured such that the fourth opening (112) is open in said first position of the valve body (132).

41. The manifold (100) according to claim 39, wherein the valve body (132) is configured such that the passage (118) and the fourth opening (112) are open in said second position; and
   the segment (132) further comprises a guide face (132") configured for conveying the fluid supply from the fourth opening (112) in a direction through the passage (118).

42. The manifold (100) according to claim 39, wherein the valve body (132) is configured such that the passage (118) and the fourth opening (112) are open in said second position; and
   the fourth opening (112) is so arranged relative to the passage (118) that the supplied fluid flows through the passage (118).

43. The manifold (100) according to claim 38, wherein the valve body (132) is configured such that the passage (118) and the fourth opening (112) are open in said second position; and
   the segment (132) further comprises a guide face (132") configured for conveying the fluid supply from the fourth opening (112) in a direction through the passage (118).

44. The manifold (100) according to claim 38, wherein the valve body (132) is configured such that the passage (118) and the fourth opening (112) are open in said second position; and
   the fourth opening (112) is so arranged relative to the passage (118) that the supplied fluid flows through the passage (118).

45. The manifold according to claim 37, wherein the valve body (132) is configured such that the fourth opening (112) is open in said first position of the valve body (132).

46. The manifold (100) according to claim 37, wherein the valve body (132) further comprises a guide face (132") configured for conveying the fluid supply from the fourth opening (112) in a direction through the passage (118).

47. The manifold (100) according to claim 46, wherein the guide face (132") forms a flow passage in combination with an interior face of the manifold (100).

48. The manifold (100) according to claim 37, wherein the valve body (132) is configured such that the passage (118) and the fourth opening (112) are open in said second position; and
   the fourth opening (112) is so arranged relative to the passage (118) that the supplied fluid flows through the passage (118).

49. The manifold (100) according to claim 37, wherein the interior manifold chamber (102) is configured as a cylindrical body interrupted by the cylindrical portion (125) that extends transversally to the axis.

50. The manifold (100) according to claim 37, wherein the first manifold portion (110) is formed integrally with the second manifold portion (140); and
   the passage (118) is defined by an area that is shared by the first section (115) and the second section (145).

51. The manifold (100) according to claim 37, wherein the first manifold portion (110) and the second manifold portion (140) constitute separate portions of the manifold;
   the first manifold portion (110) and the second manifold portion (140) comprise mutually complementary connecting means (110', 141'); and
   said complementary connecting means (110', 140') form a tight connection.

52. The manifold (100) according to claim 37, wherein, at the first opening (111), the first manifold portion (110) further comprises a peripheral surface area (1280) configured for forming a direct abutment for a compressible shrouding (50) for the catheter (40); and
   the manifold (100) further comprises a sleeve (108) configured for securing the shrouding in abutment on said surface (1280).

53. The manifold (100) according to claim 37, wherein the first manifold portion (110) and the second manifold portion (140) further comprises means (150,152), whereby it is possible to directly connect, at the second opening (141), the third opening (142) and the fourth opening (112), an endotracheal tube, a tube for ventilating the patient and a tubing for the supply of fluid, respectively.

54. The manifold (100) according to claim 37, further comprising a fifth opening (122) arranged in the cylindrical portion (125);
   wherein the valve body (132) is connected to the exterior of the manifold chamber (102) via the fifth opening (122).

55. The manifold (100) according to claim 38, wherein the valve body (132) is configured such that the fourth opening (112) is open in said first position of the valve body (132).

56. A system (1) for endotracheal ventilation and aspiration of a patient comprising a catheter (40) that extends interiorly of a collapsible shrouding (50), said system further comprising a first end (52) connected to a vacuum source, and a second end (54) connected to a manifold (100) having an interior manifold chamber (102) that defines a through-going axis through the manifold (100), said manifold (100) comprising:
   a first manifold portion (110) defining a first section (115) of the manifold chamber (102);
   a second manifold portion (140) arranged in extension of said first manifold portion (110) and defining a second section (145) of the manifold chamber (102);
   a first opening (111) arranged in the first manifold section (110) and configured for allowing advancement of a catheter for aspiration of the patient into the first section (115);
   a second opening (141) arranged in the second manifold portion (140) opposite said first opening (111) and configured for allowing advancement of the catheter from the second section (145), preferably to an endotracheal tube;
   a third opening (142) arranged in the second manifold portion (140) and configured for allowing ventilation of the patient;
   a passage (118) arranged opposite said first opening (111) and configured for allowing advancement of the catheter from the first section (115) and into the second section (145);
   a turnable valve body (132) arranged interiorly of the first section (115) and configured for being movable between a first position in which the passage (118) is blocked and a second position;
   wherein the first manifold portion (110) also defines a substantially cylindrical portion (125) that extends substantially perpendicular to the axis;
   which cylindrical portion (125) has a cylinder axis (128) about which said valve body (132) is able to turn between the first and the second position;
   a fourth opening (112) arranged in the cylindrical portion (125) and configured for allowing supply of fluid; characterised in that the valve body (132) is configured as a segment of a face of a cylinder configured for abutting on the cylindrical portion (125);
   said valve body (132) being configured such that the passage (118) and the fourth opening (112) are open in said second position to allow fluid supplied through said fourth opening (112) to flow through said passage (118) while performing suctioning of the patient by said catheter (40) advanced through said passage (118).

57. The system (1) according to claim 56, further comprising a circular guide track (103") for the valve body (132) interior to the first manifold portion (110).

58. The system (1) according to claim 57, wherein the valve body (132) further comprises an extreme end (132'); and
   the guide track (103') is configured for receiving the extreme end (132').

59. The system (1) according to claim 58, wherein the valve body (132) is configured such that the fourth opening (112) is open in said first position of the valve body (132).

60. The system (1) according to claim 58, wherein the valve body (132) is configured such that the passage (118) and the fourth opening (112) are open in said second position; and
   the segment (132) further comprises a guide face (132") configured for conveying the fluid supply from the fourth opening (112) in a direction through the passage (118).

61. The system (1) according to claim 58, wherein the valve body (132) is configured such that the passage (118) and the fourth opening (112) are open in said second position; and
   the fourth opening (112) is so arranged relative to the passage (118) that the supplied fluid flows through the passage (118).

62. The system (1) according to claim 57, wherein the valve body (132) is configured such that the fourth opening (112) is open in said first position of the valve body (132).

63. The system (1) according to claim 57, wherein the valve body (132) is configured such that the passage (118) and the fourth opening (112) are open in said second position; and
   the segment (132) further comprises a guide face (132") configured for conveying the fluid supply from the fourth opening (112) in a direction through the passage (118).

64. The system (1) according to claim 57, wherein the valve body (132) is configured such that the passage (118) and the fourth opening (112) are open in said second position; and
   the fourth opening (112) is so arranged relative to the passage (118) that the supplied fluid flows through the passage (118).

65. The system (1) according to claim 56, wherein the valve body (132) is configured such that the fourth opening (112) is open in said first position of the valve body (132).

66. The system (1) according to claim 56, wherein the valve body (132) further comprises a guide face (132") configured for conveying the fluid supply from the fourth opening (112) in a direction through the passage (118).

67. The system (1) according to claim 66, wherein the guide face (132") forms a flow passage in combination with an interior face of the manifold (100).

68. The system (1) according to claim 56, wherein the valve body (132) is configured such that the passage (118) and the fourth opening (112) are open in said second position; and
   the fourth opening (112) is so arranged relative to the passage (118) that the supplied fluid flows through the passage (118).

69. The system (1) according to claim 56, wherein the interior manifold chamber (102) is configured as a cylindrical body interrupted by the cylindrical portion (125) that extends transversally to the axis.

70. The system (1) according to claim 56, wherein the first manifold portion (110) is formed integrally with the second manifold portion (140); and
   the passage (118) is defined by an area that is shared by the first section (115) and the second section (145).

71. The system (1) according to claim 56, wherein the first manifold portion (110) and the second manifold portion (140) constitute separate portions of the manifold;

the first manifold portion (110) and the second manifold portion (140) comprise mutually complementary connecting means (110', 141'); and said complementary connecting means (110', 140') form a tight connection.

72. The system (1) according to claim 56, wherein, at the first opening (111), the first manifold portion (110) further comprises a peripheral surface area (1280) configured for forming a direct abutment for a compressible shrouding (50) for the catheter (40); and the manifold (100) further comprises a sleeve (108) configured for securing the shrouding in abutment on said surface (1280).

73. The system (1) according to claim 56, wherein the first manifold portion (110) and the second manifold portion (140) further comprises means (150,152), whereby it is possible to directly connect, at the second opening (141), the third opening (142) and the fourth opening (112), an endotracheal tube, a tube for ventilating the patient and a tubing for the supply of fluid, respectively.

74. The system (1) according to claim 56, further comprising a fifth opening (122) arranged in the cylindrical portion (125);

wherein the valve body (132) is connected to the exterior of the manifold chamber (102) via the fifth opening (122).

* * * * *